United States Patent [19]

Yelnosky et al.

[11] 4,203,983

[45] May 20, 1980

[54] SPASMOLYTIC TRIAZINONES

[75] Inventors: John Yelnosky, Warrington; George H. Douglas, Malvern; Ghulam N. Mir, Buckingham; Chong M. Won, Warrington, all of Pa.

[73] Assignee: William H. Rorer, Inc., Fort Washington, Pa.

[21] Appl. No.: 959,840

[22] Filed: Nov. 13, 1978

[51] Int. Cl.$^2$ .................... A61K 31/53; A61K 31/54; A61K 31/535
[52] U.S. Cl. .................................. 424/249; 424/246; 424/248.5; 424/248.54
[58] Field of Search ......................................... 424/249

[56] References Cited

U.S. PATENT DOCUMENTS 4,068,081  1/1978  Kay ...................... 424/249

Primary Examiner—Frederick E. Waddell
Attorney, Agent, or Firm—Ernest G. Szoke

[57] ABSTRACT

1,4-disubstituted-1,2-dihydro-1,3,5-triazin-2-ones and their pharmaceutically acceptable salts are used in the control of abdominal spasticity especially the treatment of spasmodic conditions of the gastrointestinal tract by administering an effective amount of the triazinone in suitable pharmaceutical dosage forms including oral or parenteral dosage forms compounded with pharmaceutically acceptable carrier materials to patients having spasmodic syndromes.

12 Claims, No Drawings

SPASMOLYTIC TRIAZINONES

BACKGROUND OF THE INVENTION

The present invention relates to the treatment of spasmodic syndromes with novel therapeutic compositions which relieve abdominal spasms especially spastic conditions including aypermotility in the stomach and intestines without causing any significant side effects which generally accompany the administration of spasmolytic agents. Spasmolytic agents generally in use are those which act by inhibiting the effect of acetylcholine which effect is referred to as an antimuscarinic effect. Spasmolytic agents other than antimuscarinic drugs are highly desired in order to permit the treatment of spasms without the side effects that normally accompany antimuscarinic agents, including the inhibition of gastric secretions. Because of the side effects of the antimuscarinic drugs generally employed in the treatment of spasmodic syndromes, tolerated doses do not permit the achievement of the full antispasmodic effect of the drug and those antispasmodic drugs which are less specific and therefore less antimuscarinic in nature are also less effective. It is therefore an object of the present invention to provide a non-specific antispasmodic agent which is particularly useful in supressing spasms in the smooth muscle of the gut including cholinergically induced spasms. Such spasmodic agents are particularly useful in the treatment of gastrointestinal disorders accompanied by hypermotility or abdominal cramps and find extensive application in the control of cramping and hypermotility associated with mild diarrhea.

SUMMARY OF THE INVENTION

This invention pertains to novel therapeutic compositions for relaxing abdominal smooth muscle and their use in the treatment of a variety of conditions involving tone or motility of abdominal smooth muscle, such as, gastrointestinal disorders accompanied by spasmodic symptoms such as hypermotility or abdominal cramps. The therapeutic compositions of this invention are formulated by combining an effective amount of a 1,4-disubstituted 1,2-dihydro-1,3,5-triazinone-2-one with a pharmaceutically acceptable carrier. The compositions are provided in dosage forms suitable for oral or parenteral administration. In particular, the compositions of this invention can be administered at therapeutic doses which provide a direct spasmodic action on the musculature of the gastrointestinal tract by relaxing the smooth muscle with little effect on gastric secretion and without any other detectable side effects at maximum effective dose levels. Such compositions are particularly beneficial since patient resistance to therapy due to unpleasant side effects is avoided. Thus, the compositions of this invention allow the physician wider latitude both in the amount and frequency of the prescribed dosages. Moreover, the compositions of this invention can be utilized for the treatment of mild discomfort owing to gastrointestinal spasm by providing relief for the mild disorder without a greater discomfort from side effects.

DETAILED DESCRIPTION OF THE INVENTION

The active ingredients in the spasmodic compositions of this invention are the compounds of the formula

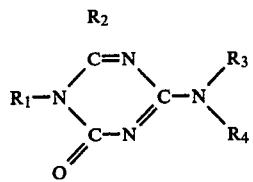

wherein $R_1$ is phenyl, benzyl or phenethyl or the same wherein the phenyl group is a 2,6-substituted phenyl or pyridyl or substituted pyridyl; $R_2$ is hydrogen or lower alkyl and $R_3$ and $R_4$ are each independently hydrogen, hydroxy, lower alkyl, lower alkoxy or halo lower alkyl or together $R_3$ and $R_4$ are a 5 or 6 membered nitrogen heterocycle which may contain 1 or 2 additional hetero atoms which may be N, S or O.

The phenyl and pyridyl substituents may be the same or different and may be lower alkyl, halo, lower alkoxy or halo lower alkyl, hydroxyl, nitro, amino, acyloxy, acylamino, cyano, carboxyl or lower alkyl sulfonyl.

The preferred substituted phenyl groups are those wherein the 2,6 positions have the same substitution which may be lower, alkyl, halo-lower alkyl or lower alkoxy, and the pharmaceutically acceptable salts.

The preferred pyridyl substituents are the 2-pyridyls, the 3-substituted 2-pyridyls, the 2,6-disubstituted 3-pyridyls, and the 2,6-disubstituted 4-pyridyls.

A particularly preferred group of spasmolytic agents useful in the practice of this invention are the compounds of the formula

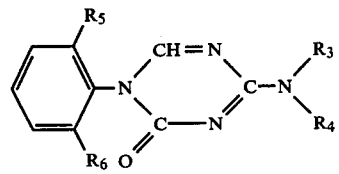

wherein $R_5$ and $R_6$ are each lower alkyl and $R_4$ is lower alkyl or alkoxy; and their pharmaceutically acceptable salts.

The triazinone derivative employed as the active ingredient of the composition of this invention are novel compounds which are disclosed and claimed in a co-pending application filed concurrently herewith and assigned to the assignee of the present application. Said copending application is entitled "TRIAZINONES" filed in the name of Douglas, Studt, Won and Dodson (application Ser. No. 959,611, filed Nov. 13, 1978). The disclosure of said depending application which describes the synthesis and identification of the compounds employed in the practice of this invention along with their properties is incorporated herein by reference.

The antispasmodic activity of the compounds of this invention has been demonstrated experimentally in animal models in tests which correlate to drug action in human patients. Based on these tests, the spasmodic agents of this invention will find use in the treatment of humans and animals suffering spasms of abdominal smooth muscle especially from gastrointestinal disorders accompanied by muscle spasms.

Test Protocols (a) Inhibition of the Gastrointestinal Transit Time of a Charcoal Meal in Mice A charcoal suspension (10 ml/kg of a 10% suspension) was given orally to groups of ten Swiss Webster male mice (18–22 g) one hour after an oral dose of test compound or vehicle. The mice were sacrificed by cervical dislocation 30 minutes after the charcoal meal and the distance in millimeters that the charcoal meal traveled through the small intestine was measured and compared to the controls.

$$\frac{\text{Mean distance in controls} - \text{mean distance in treated}}{\text{Mean distance in controls}} \times 100 = \% \text{ Inhibition}$$

(b) The Effect of Naloxone on the Inhibitory Actions of Triazinones on Gastrointestinal Motility Male Swiss Webster mice (18–20 g) in groups of ten were randomly selected for dosing with test compound or the vehicle alone and concomitantly with naloxone. The naloxone was dissolved in saline.

The mice were given a charcoal meal (10 ml/kg of a 10% suspension) one hour after an oral dose of the vehicle or a test compound(s). Thirty minutes after the charcoal meal the mice were sacrificed by cervical dislocation and the distance in millimeters that the charcoal meal traveled through the small intestine was measured and compared to the controls.

Results (a) Inhibition of the Gastrointestinal Transit Time of a Charcoal Meal in Mice Twenty mice were used as controls and ten mice at each dose level. Inhibition with a 1-(2',6'-dimethylphenyl)-4-methylamino-1,2-dihydro-1,3,5-triazin-2-one hydrochloride was dose-related.

(b) The Effect of Naloxone on the Inhibitory Actions of 1-(2,6-dimethylphenyl)-3-methylamino-1,2-dihydro-1,3,5-triazin-2-one hydrochloride Naloxone is a well-known specific antagonist of morphine-like compounds. As previously reported, diphenoxylate was antagonized by naloxone competitively in the charcoal meal test. Naloxone had no effect on the actions of 1-(2',6'-dimethyl-phenyl)-4-methylamino-1,2-dihydro-1,3,5-triazin-2-one hydrochloride. The dose of naloxone used in this test did not, by itself, change the gastrointestinal transit time of a charcoal meal.

The triazinone compounds can be administered in effective dose amounts either orally, rectally or by injection either intraperitoneally or intravenously or by injection directly into the smooth muscle of the gut. Dosage amount will generally depend on the route of administration. The most direct forms of administration for delivering the drug to the site of activity within the cell require the lowest dosage. In test animals it has been found that smooth muscle spasms can be relieved at dosage levels administered orally in amounts between about 2 mg/kg of body weight and 10 mg/kg preferably about 4 to 6 mg/kg of body weight. The particular dose will depend upon the frequency of dosage and the route of administration generally about 4 to 6 mg/kg of body weight administered 4 to 6 times daily is sufficient to maintain an active dose level which will prevent or relieve spasmodic symptoms. The ordinary single oral dose amounts for humans will vary between about 10 and 100 mg and preferably between about 5 and 50 mg. Where other routes of administration are used such as parenteral administration for example, intraperitoneal or anal administration for example, suppositories, lower or higher rates will be used in order to maintain drug level at or near its maximum effective dose. The antispasmodic activity of the compounds disclosed herein is related to antidiarrheal and antisecretory activity which effects are disclosed in copending applications entitled "ANTIDIARRHEAL TRIAZINONES" application Ser. No. 959,722, filed Nov. 13, 1978 and "ANTISECRETORY TRIAZINONES" application Ser. No. 959,950, filed Nov. 13, 1978 respectively and assigned to the same assignee. It has, however, been found that the antispasmodic effect is dose differentiated which makes these compounds particularly useful as therapeutic agents in the treatment of spasmodic symptoms without related side effects. In particular, the maximum antispasmodic effect can be achieved at dose levels well below those at which an antisecretory effect can be observed. The maximum spasmolytic dose in that amount which, when administered in a single oral dose, produces an antispasmodic effect which effect does not increase substantially in a dose related manner at higher dose amounts. Where administration is by methods other than single oral dosage, the maximum spasmolytic dose will differ, though in all cases, it is believed that a dose level can be achieved at which there are no appreciable effects other than the spasmolytic effect, and above which there is no appreciable dose related increase in the spasmolytic response. The maximum spasmolytic dose will also vary with the particular compound chosen and such other factors as age and weight and condition of the patient. Generally, it is expected that the maximum spasmolytic dose for compounds of Formula I can be obtained with doses less than about 15 mg per kg of body weight and usually at doses of about 5 mg. per kg. For most of the compounds of Formula I, the antispasmodic effect reaches a maximum at about 4 to 6 mg/kg administered orally after which there is little or no increased effectiveness from higher dose rates and therefore, the response is not dose related above its maximum effective dose. The maximum effective dose will, of course, vary depending upon the particular patient, route of administration and causative factors for the spasmodic symptoms.

The therapeutic composition of the invention appears to exert a non-specific antispasmodic effect with no observed anticholinergic effect and little or no other side effects. These compositions are particularly useful in the control of intestinal hypermotility and similar conditions involving excessive smooth muscle contraction. Since the compounds exert their maximum effect at doses clearly below tolerated dose levels and significantly below levels at which other effects are produced, they are particularly useful in controlling mild spasmodic conditions associated with such disorders as dysentary, spastic colitis and diverticulitis where the compound can be used to control both the associated abdominal cramps and can also be used for the control of functional spasm of the gastrointestinal tract.

In general, symptomatic relief of muscle spasm arising out of gastrointestinal disorders or other human abdominal smooth muscle spasm can be relieved by the compositions of this invention at doses well below the maximum tolerated dose. Unlike most antispasmodic drugs which are used clinically, the compositions of this invention produce a non-specific relaxant action. The compositions can be used in a wide variety of conditions involving increased tone or motility of the gastrointestinal tract. The compositions reduce tone and amplitude and decrease motility at maximum effective dose which is well below the maximum tolerated dose, and produce a real effect on any condition which is caused by excessive smooth muscle contraction. In general, the spasmolytic agents of this invention can be used to produce smooth muscle flacidity either as a treatment or prophylactically or in conjunction with other therapy. The therapeutic compositions of this invention, when used to treat conditions which are known to respond to available antispasmodic drugs such as papaverine or theophylline, will find broad applications by analogy to such agents. If desired, the active triazinones of this invention can be used in combination with other drugs intended for treatment of the conditions which give rise to the spasmodic syndromes. Based upon the pharmacological results in animal models, the compositions of this invention are predictably useful in human therapeutics for the treatment of spasmodic symptoms without regard to etiology. However, depending upon the cause, the compositions may be formulated to include other therapeutically active ingredients along with the spasmolytic agents described above. Such other ingredients include for example, CNS active agents, compounds affecting body fluids or electrolyte levels or locally acting drugs.

The compositions of the present invention can be prepared in forms suitable for administration to humans and animals by compounding an effective single dose amount of a compound of Formula I with known ingredients generally employed in the preparation of therapeutic compositions provided as tablets, capsules, lozenges, chewable lozenges, pills, powder, granules, suspensions, oil-in-water or water-in-oil emulsions, or other similar forms which can be taken orally. Since the compounds are readily absorbed into the blood stream from the stomach and intestines when taken orally, the preferred method of treatment is to give the drug orally which is also the safest and most practical route of administration. Optional methods can be used. Where, for example, the patient cannot swallow or has difficulty in swallowing, other methods of administration which permit the drug to be absorbed from the gastrointestinal tract or which deliver a solution of the drug directly to the blood stream can be employed.

In general, compounds of Formula I above are indicated for use as pharmacotherapeutic agents in a wide variety of mammalian conditions which require spasmolytic relief either remedially or prophylactically or in combination with other therapy including treatments which cause excessive or unusual smooth muscle spasms or hyperactivity as an undesired side effect.

The dosage regimens in carrying out the pharmacotherapeutic methods utilizing the triazine composition of this invention are those which insure maximum therapeutic response until improvement is obtained and thereafter the minimum effective level which gives relief. Thus, in general, the dosages are tose that are therapeutically effective in the treatment of spasms. In general, the single oral dose will contain between about 10 mg and 100 mg (preferably in the range of 5 to 50 mg) Fractional or multiple doses can of course be given bearing in mind that in selecting the appropriate dosage in any specific case, consideration must be given to the patient's weight, general health, age, and other factors which may influence response to the drug. The drug response on oral administration usually follows within 10 to 30 minutes after administration and is maintained for 1 to 4 hours. The drug is generally given in single doses 2 to 6 times daily or as required to maintain an effective drug level in the blood stream for continuous suppression of secretory action. In general, effective levels can be maintained by administering about 5 to 10 mg per kg of body weight every 4 to 6 hours. The dose level varies with other routes of administration such as parenteral or anal. Alternatively, the drug can be administered by formulations which provide sustained release at active levels. The spasmolytic effect is dose related up to the maximum effective dose though a minimum dose of about 2 mg/kg is ordinarily required to produce a useful effect and the maximum effect is usually achieved at doses well below the maximum tolerated dose.

Compositions intended for oral use may be prepared according to methods known generally in the art. Such compositions may contain one or more agents selected from the group consisting of sweetening agents, flavoring agents, coloring agents and preserving agents, in order to provide a pharmaceutically elegant and palatable preparation. Orally, they may be administered in tablets, lozenges, aqueous or oily suspensions, dispersible powders or granules, emulsions, hard or soft capsules, or syrups or elixers which contain the active triazine ingredient in admixture with non-toxic pharmaceutically acceptable excipients. Excipients which may be, for example, inert diluents, such as calcium carbonate, sodium carbonate, lactose, calcium phosphate or sodium phosphate; granulating and disintegrating agents, for example, starch, gelatin, or acacia; and lubricating agents, for example, magnesium stearate, stearic acid or talc. The tablets may be uncoated or they may be coated by known techniques to make them more effective, for example, to delay disintegration or absorption or to make them more palatable or for other reasons for which orally administered drugs have been previously provided in coated form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions containing the active triazine form a further embodiment of this invention. Excipients suitable for aqueous suspensions may be employed, if desired. These excipients are suspending agents, for example, sodium carboxymethyl-cellulose, methyl-cellulose, hydroxypropyl-methylcellulose, sodium alginate, polyvinylpyrrolidine, gum tragacanth and gum acacia; dispersing or wetting agents may be a naturally ocurring phosphatide, for example, lecithin; or condensation products or an alkylene oxide with fatty acids, for example, polyoxyethylene stearate; or condensation products of ethylene oxide with long-chain aliphatic alcohols, for example, heptadecaethyleneoxy-cetanol; or condensation products of ethylene oxide with partial esters derived from fatty acids and a hexitol, for example, polyoxyethylene sorbitol mono-oleate; or condensation products of ehtylene oxide with partial esters derived from fatty acids and hexitol anhydrides, for example, polyoxyethylene sorbitan monoleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents may also be present.

The compounds of this invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occuring gums, for example, gum acacia or gum tragacanth, naturally-occuring phosphatides, for example, soya bean lecithin, and esters or partial esters derived from fatty acids and hexitol anhydrides, for example, sorbitan mono-oleate. The emulsions may also contain sweetening and flavoring agents.

Syrups and elixers may be formulated with sweetening agents, for example, glycerol, sorbitol or sucrose. Such formulations may also contain a demulcent, a preservative and flavoring and coloring agents. The pharmaceutical compositions may be in the form of a sterile injectable preparation, for example, as a sterile injectable aqueous suspension. This suspension may be formulated according to the known art using those suitable dispersing or wetting agents and suspending agents which have been mentioned above. The sterile injective preparation may also be a sterile injectable solution or suspension in a non-toxic parenterally-acceptable diluent or solvent, for example, as an aqueous solution buffered to a pH of 4.0 to 7.0 and made isotonic with sodium chloride.

Further, the active triazine may be administered alone or in admixture with other agents having the same or different pharmacological properties.

Generally, these compounds may be tableted or otherwise formulated for oral use so that for every 100 parts by weight of the composition, there are present between 5 and 95 parts by weight of the active ingredient.

The following examples are given by way of illustrating the preparation of the active triazinones used in the method and compositions of this invention. Novel therapeutic compositions are also exemplified. It will be understood that variations in amounts and adjuvants used in compounding suitable compositions can be made without departing from the teaching of this invention which is the administration of a 1,4-disubstitituted-1,2-dihydro-1,3,5-triazin-2-one of Formula I in a manner and in amounts sufficient to provide and maintain an effective level in the G.I. tract for either prophylactic or therapeutic relief of spasms. If desired, the compounds can be formulated with other active ingredients or administered with other drugs or as part of a program of therapy that includes suppression of gastrointestinal secretion. The salts of compounds of Formula I including acid addition salts and quarternary ammonium salts are particularly suitable for preparing pharmaceutical compositions. The acid addition salts of strong acids such as the hydrochloride, the hydrobromide, sulfate, nitrate, phosphate, methane sulfonate, benzene sulfonate and the like are especially useful. The salts of any strong Lewis acids can be used.

EXAMPLE 1

Preparation of
1-(2',6'-dimethylphenyl)-4-methylamino-1,2-dihydro-1,3,5-triazin-2-one About 200 mg of 1-(2,6-dimethylphenyl)-3-amidinourea hydrochloride was introduced in a gas chromatograph hypo vial and dissolved in 1 ml of acetonitrile. To the solution was added 0.2 ml of DMF DMA reagent. The vial was sealed with crimper and heated at 105° C. for 15 minutes in an oven. Seven vials were made. The contents of the vials were then put into a long-neck round bottom flask and evaporated to dryness by a flask evaporator. The solid mass was dissolved in a mixture of 30 ml of CHCl$_3$ and 20 ml of water and shaken vigorously in a 60 ml separatory funnel. The aqueous layer was discarded and 20 ml of water was added and shaken. The CHCl$_3$ layer was then taken and about 10 g of anhydrous Na$_2$SO$_4$ was added, the CHCl$_3$ solution was decanted into a flask and evaporated to dryness. The solid material was dissolved in pentanone-2 (about 80 ml) at 70° C. The solution was concentrated and crystallized upon cooling. The crystals were collected and dried in a desiccator with P$_2$O$_5$ with vacuum for one hour.

|  | MW: 230.26 | | MP: 225–226° C. |
|---|---|---|---|
| Elemental Analysis | C | H | N |
| Calculated | 62.59 | 6.13 | 24.33 |
| Found | 62.84 | 6.15 | 24.28 |

EXAMPLE 2

Preparation of
1-(2',6'-diethylphenyl)-4-methylamino-1,2-dihydro-1,3,5-triazin-2-one The same procedure was followed as in Example 1 above using 1-(2,6-diethylphenyl)-3-methylamidinourea as the starting material and using as the recrystallization medium a mixed solvent of pentanone and hexane (30:10).

|  | MP: 210–211° C. | | |
|---|---|---|---|
| Elemental Analysis | C | H | N |
| Calculated | 65.09 | 7.02 | 21.89 |
| Found | 65.34 | 7.01 | 21.83 |

EXAMPLE 3

1-(2',6'-dimethylphenyl)-4-methylamino-1,2-dihydro-1,3,5-triazin-2-one-hydrochloride To a suspension of 10.0 g (30.0 m mole) of 1-(2,6-dimethylphenyl)-3-methylamidinourea hydrochloride in acitonitrile (CH$_3$CN) (50 ml) was added 9.3 g (78.0 m mol) of dimethylformamide dimethylacetal (DMF-DMA) and the resulting solution in a bomb was heated to 100°–105° C. for one hour. After cooling, the reaction mixture was placed in a round bottom flask and concentrated under reduced pressure. The residue was partitioned between H₂O and CHCl₃ and the layers separated. The aqueous layer was extracted with CHCl₃ (1×50 ml). The combined CHCl₃ extracts were washed with H₂O (1×50 ml) dried (MgSO₄) and concentrated under reduced pressure. A small amount of the residue was triturated in hexanes to give a white solid, having melting point 224 NMR and IR showed the product to be identical with that of Example 3. The remainder of the residue was dissolved in MeOH and acidified with HCl/MeOH. The MeOH was removed under vacuum and the residue crystallized from CH₃CN to give 6.8 g of 1-(2,6-dimethylphenyl)-4-methylaminotriazin-2(6H)-one hydrochloride, melting point 234°–8° C. (decomposition).

| Analysis calculated for: $C_{12}H_{15}ClN_4O$ | | | |
|---|---|---|---|
| | C | H | N | Cl |
| Calculated: | 54.04 | 5.67 | 21.01 | 13.29 |
| Found: | 54.14 | 5.80 | 21.90 | 13.28 |

1-(2',6'-dimethylphenyl)-4-methylamino-1,2-dihydro-1,3,5-triazin-2-one methanesulfonate A solution of 6.0 g (0.026 moles) of 1-(2,6-dimethylphenyl)-4-methylamino-dihydro-1,3,5-triazin-2-one in 100 ml iPA was prepared with warming. To the warm solution was added 2.0 ml (0.031 moles) of methane-sulfonic acid. The mixture became hot and crystals of white crystalline solid began to form almost immediately. The mixture allowed to cool to room temperature in tap water and filtered. The solution was washed with iPA EtOH to give 8.00 g of product which was dried overnight at 50°–60° C. in a vacuum. Obtained 8.0 g of 1-(2,6-dimethylphenyl)-4-methylaminodihydro-1,3,5-triazin-2-one methanesulfonate after drying.

| Calculated for: $C_{13}H_{18}N_4O_4S$ | MW: 326.35 | | MP: 262–65° C. dec. |
|---|---|---|---|
| | C | H | N | S |
| Calculated: | 47.84 | 5.57 | 17.17 | 9.80 |
| Found | 48.03 | 5.71 | 17.25 | 10.27 |

EXAMPLE 5

1-(2',6'-diethylphenyl)-4-methylamino-1,2-dihydro-1,3,5-triazin-2-one hydrochloride To a suspension of 22.8 g (80.0 mmol) of 1-(2,6-diethylphenyl)-3-methylamidinourea hydrochloride in CH₃CN (100 ml) were added 19.1 g (160.0 mmol) of DMF-DMA and the reaction mixture was heated at reflux for 3 hours. The CH₃CN was removed under reduced pressure and the residue partitioned between CHCl₃ and H₂O. The layers were separated and the aqueous layer extracted with CHCl₃ (1×100). The combined CHCl₃ extracts were washed with H₂O (1×100 ml), dried (MgSO₄) and concentrated under reduced pressure to give an off-white solid, which by NMR confirmed the desired free base. The solid was dissolved in CH₃CN and acidified with HCl/MeOH and the MeOH removed under reduced pressure to give an off-white solid which was crystallized from CH₃CN to give after vacuum drying (105° C., house vacuum) 16.7 g of crude product. The material was recrystallized from CH₃CN (a hot filtration was necessary to remove some undissolved solid) to give 11.0 g of desired product as a white crystalline solid:

| Analysis calculated for: $C_{14}H_{18}N_4O \cdot HCl$ | | | MP: 208–15° C. |
|---|---|---|---|
| | C | H | N | Cl |
| Calculated: | 57.04 | 6.50 | 19.01 | 12.03 |
| Found: | 57.14 | 6.51 | 19.38 | 12.01 |

EXAMPLE 6

4dimethylamino-1-(2',6'-dimethylphenyl)-1,2-dihydro-1,3,5-triazin-2-one hydrochloride To a suspension of 19.0 g (0.07 mole) of 1-(2,6-dimethylphenyl)-3-(N,N-dimethyl)-amidinourea in acetonitrile (100 m) were added 16.7 g (0.14 mole) of DMF-DMA and the mixture refluxed for 2 hours. The acetonitrile was removed under reduced pressure and the residue partitioned between H₂O and CHCl₃. The layers were separated and the aqueous layer extracted with CHCl₃ (1×100 ml). The CHCl₃ extracts were washed with H₂O (1×50 ml), dried over MgSO₄ and concentrated at reduced pressure to give an oil. Trituration of the oil in EtOH precipitated a white solid which was filtered and washed with EtOH to give the desired product after air drying. The solid was dissolved in MeOH and acidified with HCl/MeOH. The MeOH was removed under reduced pressure to give a white solid which was triturated with CH₃CN, filtered and washed with CH₃CN to give 7.5 g of product which by NMR seemed to be a hydrate or wet. The solid was vacuum dried for 6 hours at 100° C. under vacuum.

| Analysis calculated for: $C_{13}H_{10}N_4O \cdot HCl$ | | | |
|---|---|---|---|
| | C | H | N | Cl |
| Calculated: | 55.61 | 6.10 | 19.96 | 12.63 |
| Found: | 55.81 | 5.96 | 20.31 | 12.46 |

EXAMPLE 7

Therapeutic compositions of the invention are prepared by using known techniques for compounding employing either the base or a salt as the active ingredient along with the non-toxic excipients chosen in accordance with the particular form and properties desired for the therapeutic composition.

Tablets which can be advantageously used to inhibit or suppress gastrointestinal secretions to prevent or treat conditions associated with excessive secretory action can be provided in a form which reduces the total secretion when taken at a rate of 4 to 6 tablets per day containing between about 200 to 1000 mg of the active ingredient. An exemplary formulation which can be utilized is, for example, the following.

| | |
|---|---|
| 1-(2'6'-dimethylphenyl)-4-methylamino-1,2-dihydro-1,3,5-triazin-2-one | 500 mg. |
| tricalcium phosphate | 200 mg. |
| talc | 50 mg. |
| magnesium stearate | 10 mg. |
| polyvinyl acetate | 40 mg. |

In addition, there are added protective excipients such as ethylcellulose, dibutylphthalate, propylene glycol, wax (white and/or carbauba), spermaceti, methylene chloride, and rectified diethyl ether. The ingredients are compressed to minimum size to provide a tablet of about 850 mg.

EXAMPLE 8

A lot of 1,000 tablets each containing 1 g of 1-(2'6'-diethylphenyl)-4-methylamino-1,2-dihydro-1,3,5-triazin-2-one is prepared from the following types and amounts of ingredients:

| | |
|---|---|
| 1-(2'6'-diethylphenyl)-4-methylamino-1,2-dihydro-1,3,5-triazin-2-one | 1 kg. |
| dicalcium phosphate | 1 kg. |
| methylcellulose USP | 75 g. |
| talc | 150 g. |
| cornstarch | 200 g. |
| magnesium stearate | 10 g. |

The active ingredient and dicalcium phosphate are mixed thoroughly and granulated with a 7.5% solution of methylcellulose in water and passed through a #8 screen and air-dried. The dried granules are passed through a #12 screen and combined with the talc, starch and magnesium stearate with thorough mixing after which the composition is compressed into tablets.

EXAMPLE 9

A lot of 2-piece hard gelatin capsules, each containing 500 mg. of 1-(2'6'-dimethylphenyl)-4-methylamino-1,2-dihydro-1,3,5-triazin-2-one are prepared from the following types and amounts of ingredients (the amounts given are per capsule):

| | |
|---|---|
| 1-(2'6'-dimethylphenyl)-4-methylamino-1,2-dihydro-1,3,5-triazin-2-one | 500 mg. |
| dicalcium phosphate | 500 mg. |
| talc | 150 mg. |
| magnesium stearate | 5 mg. |

The ingredients are mixed thoroughly and filled into capsules which are used for oral administration at the rate of about one every four hours. If desired, slow release forms can be provided or delay release forms depending on choice of capsules and formulating ingredients.

EXAMPLE 10

A sterile solution suitable for intramuscular or interperitoneal injection, and containing 10 mg. of 1(2'6'-dimethylphenyl)-4-methylamino-1,2-dihydro-1,3,5-triazin-2-one hydrochloride in each, 10 ml. (1:1 wt./volume), is prepared from the following ingredients:

| | |
|---|---|
| 1-(2'6'-dimethylphenyl)-4-methylamino-1,2-dihydro-1,3,5-triazin-2-one hydrochloride | 10 g. |
| benzyl benzoate | 100 ml. |
| methylparaben | 1 g. |
| propylparaben | 0.5 g. |
| cottonseed oil q.s. | 500 ml. |

EXAMPLE 11

Ten thousand tablets for oral use, each containing 50 mg. of 1-(2'6'-dimethylphenyl)-4-methylamino-1,2-dihydro-1,3,5-triazin-2-one, are prepared from the following types and amounts of material:

| | |
|---|---|
| 1-(2'6'-dimethylphenyl)-4-methylamino-1,2-dihydro-1,3,5-triazin-2-one | 500 g. |
| Lactose U.S.P. | 350 g. |
| Potato Starch U.S.P. | 346 g. |

The mixture is moistened with an alcoholic solution of 20 g. of stearic acid and granulated through a sieve. After drying, the following ingredients are added:

| | |
|---|---|
| Potato Starch U.S.P. | 320 g. |
| Talc | 400 g. |
| Magnesium stearate | 500 g. |
| Colloidal silicium dioxide | 64 g. |

The mixture is thoroughly mixed and compressed into tablets.

EXAMPLE 12

Five hundred ampoules each with two ml. of solution which contain 15 mg. of 1-(2'6'-dimethylphenyl)-4-methylamino-1,2-dihydro-1,3,5-triazin-2-one is prepared from the following types and amounts of materials:

| | |
|---|---|
| 1-(2'6'-dimethylphenyl)-4-methylamino-1,2-dihydro-1,3,5-triazin-2-one | 7.5 g. |
| Ascorbic acid | 1 g. |
| Sodium bisulphite | 0.5 g. |
| Sodium sulphite | 1 g. |

EXAMPLE 13

Capsules are prepared as follows:
15 g. of 1-(2'6'-dimethylphenyl)-4-methylamino-1,2-dihydro-1,3,5-triazin-2-one,
3 g. magnesium stearate,
2 g. of finely divided silica sold under the trademark CAB-O-SIL by Godfrey L. Cabot, Inc., Boston, MA, and
369 g. of lactose.

The ingredients are thoroughly mixed with each other and the mixture is filled in gelatin capsules. Each capsule contains 500 mg. of the composition and thus, 15 mg. of 1-(2'6'-dimethylphenyl)-4-methylamino-1,2-dihydro-1,3,5-triazine-2-one.

EXAMPLE 14

50 g. of 1-(2'6'-dimethylphenyl)-4-methylamino-1,2-dihydro-1,3,5-triazin-2-one, 5 g. of propyl p-hydroxybenzoate are dissolved and dilluted to 5000 cc. with twice distilled water after the addition of modified Sorensen buffer solution in an amount sufficient to adjust the pH-value to a pH of 6.0. Sodium chloride is dissolved therein in an amount sufficient to render the resulting solution isotonic. The final solution is passed through a bacteriological filter and the filtrate is autoclaved at 120° C. for 15 minutes to yield a parenterally applicable solution which contains 50 mg. of 1-(2'6'-dimethylphenyl)-4-aminomethyl-1,2-dihydro-1,3,5-triazin-2-one in 5 cc.

EXAMPLE 15

By analogous procedures, other 1,4-disubstituted-1,2-dihydro-1,3,5-triazin-2-ones can be prepared from the corresponding amidinourea starting materials, and formulated for either oral administration, as injectible or infusible solutions or for rectal administration for example, suppository form.

Illustrative compounds which can be used as active ingredients in the therapeutic compositions of this invention prepared and formulated in accordance with the methods described herein, are the following:

1-(2'6-diethylphenyl)-4-methylamino-1,2-dihydro-1,3,5-triazin-2-one
1-(2'6'-dimethylphenyl)-4-methylamino-1,2-dihydro-1,3,5-triazin-2-one-hydrochloride
1-(2'6'-dimethylphenyl)-4-methylamino-1,2-dihydro-1,3,5-triazin-2-one methanesulfonate
1-(2'6'-diethylphenyl)-4-methylamino-1,2-dihydro-1,3,5-triazin-2-one hydrochloride
4-dimethylamino-1-(2'6'-dimethylphenyl)-1,2-dihydro-1,3,5-triazin-2-one hydrochloride
1-(2-chloro-6-methylphenyl)-4-methylamino-1,2-dihydro-1,3,5-triazin-2-one
1-(2'6'-dimethylphenyl)-4-n-butoxyamino-1,2-dihydro-1,3,5-triazin-2-one
1-(2'6'-dimethylphenyl)-4-sec-butoxyamino-1,2-dihydro-1,3,5-triazin-2-one
4-methylamino-1-phenyl-1,2-dihydro-1,3,5-triazin-2-one hydrochloride
1-(2-methylphenyl)-4-ethylamino-1,2-dihydro-1,3,5-triazin-2-one
1-(2'6'-dichlorophenyl)-4-methylamino-1,2-dihydro-1,3,5-triazin-2-one
1-(2-methylphenyl)-4-methylamino-1,2-dihydro-1,3,5-triazin-2-one
1-(2'6'-dimethylphenyl)-4-(2,2,2-trifluoroethylamino)-1,2-dihydro-1,3,5-triazin-2-one
1-(2-bromo-6-methylphenyl)-4-methylamino-1,2-dihydro-1,3,5-triazin-2-one
1-(2'6'-dimethylphenyl)-4-methoxyamino-1,2-dihydro-1,3,5-triazin-2-one hydrate
1-(2'6'-diethylphenyl)-4-propylamino-1,2-dihydro-1,3,5-triazin-2-one
1-(2'6'-diethylphenyl)-4-i-propylamino-1,2-dihydro-1,3,5-triazin-2-one
1-(2'6'-diethylphenyl)-4-propargylamino-1,2-dihydro-1,3,5-triazin-2-one
1-(2'6'-diethylphenyl)-4-cyclopropylamino-1,2-dihydro-1,3,5-triazin-2-one
1-(2'6'-diethylphenyl)-4-(N-pyrrolidinyl)-1,2-dihydro-1,3,5-triazin-2-one
1-(2'6'-diethylphenyl)-4-(N-piperidyl)-1,2-dihydro-1,3,5-triazin-2-one
1-(2'-methyl-6'-ethylphenyl)-4-methylamino-1,2-dihydro-1,3,5-triazin-2-one
1-(2'-methyl-6'-ethylphenyl)-4-(N,N-dimethylamino)-1,2-dihydro-1,3,5-triazin-2-one
1-(2'-methyl-6'-chlorophenyl)-4-methylamino-1,2-dihydro-1,3,5-triazin-2-one
1-(2'-methyl-6'-ethylphenyl)-4-(N-morpholinyl)-1,2-dihydro-1,3,5-triazin-2-one
1-(2'-methyl-6'-chlorophenyl)-4-(N-piperidinyl)-1,2-dihydro-1,3,5-triazin-2-one
1-(2'6'-dimethylphenyl)-4-[N-(3-thiomorpholinyl)]-1,2-dihydro-1,3,5-triazin-2-one
1-(2'6'-dimethylphenyl)-4-[N-(thioazolinyl)]-1,2-dihydro-1,3,5-triazin-2-one
1-(2'-chloro-6'-bromophenyl)-4-methylamino-1,2-dihydro-1,3,5-triazin-2-one
1-(2'6'-dichlorophenyl)-4-amino-1,2-dihydro-1,3,5-triazin-2-one
1-(2'-pyridyl)-4-methylamino-1,2-dihydro-1,3,5-triazin-2-one
1-(2'-pyridyl)-4-ethylamino-1,2-dihydro-1,3,5-triazin-2-one
1-(3'-ethylpyrid-2-yl)-4-ethylamino-1,2-dihydro-1,3,5-triazin-2-one
1-(3'methyl-2-pyrid-2-yl)-4-methylamino-1,2-dihydro-1,3,5-triazin-2-one
1-(3'5'-dimethylpyrid-4-yl)-4-methylamino-1,2-dihydro-1,3,5-triazin-2-one
1-(2'4'-dimethylpyrid-3-yl)-4-methylamino-1,2-dihydro-1,3,5-triazin-2-one
1-(2'6'-dimethylbenzyl)-4-methylamino-1,2-dihydro-1,3,5-triazin-2-one
1-(2'6'-dimethylphenethyl)-4-methylamino-1,2-dihydro-1,3,5-triazin-2-one

We claim:

1. A method for treating smooth muscle spasms which comprises administering to a patient in need of such therapy by oral, parenteral or anal routes an effective amount of an antispasmodic agent of the formula:

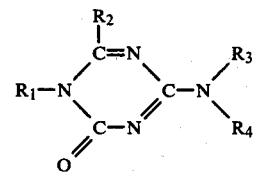

wherein $R_1$ is phenyl, benzyl or phenethyl; or phenyl, benzyl or phenethyl in which one or more of the phenyl hydrogens are substituted by lower alkyl, lower alkoxy, halo, halo-lower alkyl, amino, nitro, hydroxy, cyano, carboxyl or lower alkyl sulfonyl; pyridyl or pyridyl in which one or more of the hydrogens is replaced by lower alkyl, lower alkoxy, halo, halo-lower alkyl, amino, nitro, hydroxy, cyano, carboxyl or lower alkyl sulfonyl; $R_2$ is hydrogen or lower alkyl, and $R_3$ and $R_4$ are each independently selected from the group consisting of hydrogen, hydroxyl, lower alkanoyl, lower alkyl, lower alkenyl, lower alkynyl, lower alkoxy, halo lower alkyl, hydroxy lower alkyl, lower alkoxy lower alkyl, phenoxy lower alkyl, di-lower alkyl-amino lower alkyl; and their pharmaceutically acceptable salts.

2. A method according to claim 1 wherein the antispasmodic agent is a compound of the formula:

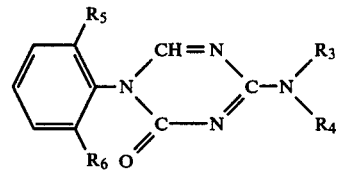

wherein $R_3$ and $R_4$ are independently selected from the group consisting of hydrogen, lower alkyl, hydroxyl, or lower alkoxy and $R_5$ and $R_6$ are each independently selected from the group consisting of hydrogen, halo, lower alkyl, lower alkoxy or halo lower alkyl; and their pharmaceutically acceptable salts.

3. A method according to claim 2 wherein the antispasmodic agent is a compound of the formula:

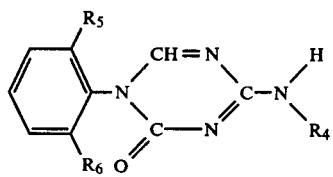

wherein R₄ is lower alkyl or lower alkoxy and R₅ and R₆ are each independently lower alkyl or lower alkoxy; and their pharmaceutically acceptable salts.

4. A method according to claim 3 wherein R₅ and R₆ are both the same and are both lower alkyl.

5. A method according to claim 4 wherein R₄ is lower alkyl.

6. A method according to claim 5 wherein each of R₅ and R₆ is methyl or ethyl.

7. A method according to claim 2 wherein the antispasmodic agent is in a dosage unit form suitable for oral administration.

8. A method according to claim 7 wherein the amount of the antispasmodic compound is between about 200 and about 500 mg.

9. A method for providing relief of mild spasms of smooth muscle in mammalian species which comprises administering to a patient in need of such therapy an oral dose of a therapeutic composition containing an effective amount of an antispasmodic agent of the formula:

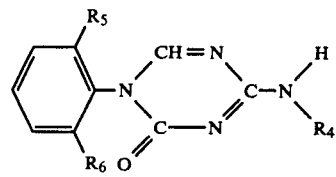

wherein R₄ is lower alkyl or lower alkoxy and R₅ and R₆ are each independently lower alkyl or lower alkoxy; and their pharmaceutically acceptable salts.

10. A method according to claim 9 wherein the dose is the maximum effective spasmolytic dose.

11. A method according to claim 10 wherein the amount of the antispasmodic agent is between about 200 and 500 mg administered every 4 to 6 hours.

12. A method for producing smooth muscle flacidity in mammalian species without any central nervous system or anticholinergic effect which comprises administering to a patient in need of such therapy an effective amount of a compound of the formula:

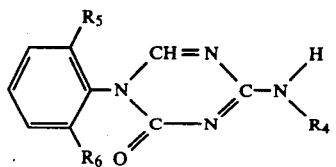

wherein R₄ is lower alkyl or lower alkoxy and R₅ and R₆ are each independently lower alkyl or lower alkoxy; and their pharmaceutically acceptable salts.

* * * * *